United States Patent [19]

Walker et al.

[11] 4,348,115

[45] Sep. 7, 1982

[54] CHROMATOGRAPHIC ANALYZER DETECTOR AND METHOD

[75] Inventors: Starnes E. Walker, Bartlesville; Fred T. Klein, Tulsa, both of Okla.

[73] Assignee: Phillips Petroleum Company, Bartlesville, Okla.

[21] Appl. No.: 121,763

[22] Filed: Feb. 15, 1980

[51] Int. Cl.³ .......................................... G01N 21/01
[52] U.S. Cl. .................................................. 356/436
[58] Field of Search ............... 356/435, 436, 439, 440, 356/441, 442, 223, 410, 411; 250/575, 578

[56] References Cited

U.S. PATENT DOCUMENTS

| | | | |
|---|---|---|---|
| 3,489,906 | 1/1970 | Beer | 356/435 X |
| 3,522,725 | 8/1970 | Waters | 73/61.1 |
| 3,591,801 | 7/1971 | Watson | 356/435 |
| 3,989,948 | 11/1976 | Allington | 250/575 |
| 4,019,372 | 4/1977 | Parkell et al. | 73/61.1 C |

OTHER PUBLICATIONS

Spectra Physics Catalog, pp. 3221–3224, Model SP8200, Dual Beam UV/Visible Detector.
Waters Associates Catalog, pp. 3451–3461 passim, Model 440 Absorbance Detector (1975).
Optichrom ® LC Process Liquid Chromatograph System, Applied Automation Inc., 1S875, DWO S940 8/78.
Burr Brown 4127 Logarithmic Amplifier (1976).

*Primary Examiner*—John K. Corbin
*Assistant Examiner*—Bruce Y. Arnold

[57] ABSTRACT

An optical absorbance detector which can be used in process chromatographic analyzers is provided. Improvements are provided in noise reduction, temperature stability, operator convenience and construction. Noise reducing features include electrical signal filtering and optical system alignment. Temperature stability features include an electronic preamplifier inside the oven and a temperature controller to maintain an integrated circuit at a constant temperature. Operator conveniences include built-in calibration for electronic circuits and easy optical filter replacement. Construction features include explosion resistance and small size.

33 Claims, 9 Drawing Figures

CHROMATOGRAPHIC ANALYZER DETECTOR AND METHOD

FIELD OF THE INVENTION

The invention relates to chromatography. In one aspect, the invention relates to an optical analyzer detector which can be used in chromatography. In another aspect, the invention relates to an optical analyzer detector suitable for use in process chromatographic analysis.

BACKGROUND OF THE INVENTION

A chromatographic analyzer is an analytical instrument used to separate in time and individually detect the constituents of a sample to be analyzed. The chromatographic analyzer typically includes an analytical column through which at least a carrier fluid stream is passed continuously. The sample to be analyzed is introduced into the carrier fluid stream and is thus carried through the analytical column. The sample constituents are carried through the analytical column at different rates and in this manner the sample constituents are separated in time.

A detector is employed to detect the separated constituents and the detector output signal is typically recorded as a function of time by a recorder to produce a chromatogram. As each sample component is eluted from the column, the component typically produces an increase in the detector output signal amplitude which appears as a peak or spike on the chromatogram.

There are many different types of chromatographic analyzer detectors. Generally, chromatographic analyzer detectors have a sample side and a reference side. Carrier fluid flows through the reference side. Carrier fluid containing an injected sample flows through the sample side. Some characteristic such an optical absorbance or transmission, electrical conductivity, or refractive index of the carrier alone is compared to the same characteristic of the carrier containing the sample to produce a difference signal. The detector output signal amplitude is representative of the difference signal and therefore permits analysis of the individual components of the sample.

An optical absorbance detector achieves chemical analysis by absorption spectroscopy in which radiation of various wavelengths is passed though a material and the radiation transmitted, or absorbed, is measured to determine material identity and concentration. Where analysis only of components absorbing at a specific wavelength is desired, this can be accomplished by using light sources emitting only specific wavelengths and/or interference filters to pass only the desired wavelengths.

One source of error in optical absorbance detectors can be error arising from refractive index effects. The refractive index effects can arise from temperature changes produced by absorption of light in optical flow cells of optical absorbance detectors. Such refractive index effects are disclosed, for example, in U.S. Pat. No. 4,019,372 which also discloses temperature control means for reducing refractive index error. Refractive index effect error can also arise from the optics of the optical absorbance detector. Accordingly, means for reducing refractive index error whether arising from temperature changes or from the optics of the optical absorbance detector are highly desirable.

Other sources of error can arise because of stray light effects and/or light crossover or crosstalk between a reference light beam and a sample light beam in an optical absorbance detector as well as from temperature variation within the optical absorbance detector which can influence electrical signals produced by the detector.

Use of chromatographic analyzers having optical absorbance detectors for continuous process monitoring and/or control places stringent constraints upon the process detector. The process detector must be suitable for use under conditions found in process applications. These conditions can include temperature extremes, the presence of explosive gases, and the like. The process detector must be rugged and capable of safe operation under such conditions and at the same time provide the sensitivity, board linear dynamic range, and long term stability necessary for process control.

Accordingly, an object of the present invention is an optical absorbance detector having an extended linear dynamic range. Another object is a ruggedized optical absorbance detector which can provide the sensitivity, linear dynamic range, and long term stability required for process applications. A further object is an optical absorbance detector capable of selectable multi-wavelength operation which can provide the sensitivity, linear dynamic range, and long term stability required for process applications. Yet another object is an optical absorbance detector with minimal refractive index error. Another object is an optical absorbance detector having minimal error resulting from stray light or light crossover. Another object is an optical absorbance detector having minimal error resulting from temperature variation. Yet another object is an optical absorbance detector with minimal refractive index error. Another object is an optical absorbance detector having minimal error resulting from stray light or light crossover. Yet other objects of the present invention include chromatographic analyzer systems utilizing such optical absorbance detectors. Other objects and advantages will be apparent to one of ordinary skill in the art from the following disclosure and the drawings in which:

FIG. 9 is a perspective view of a flow cell in accordance with the present invention having portions broken away to show structure.

BRIEF DESCRIPTION OF THE INVENTION

Figure 1:
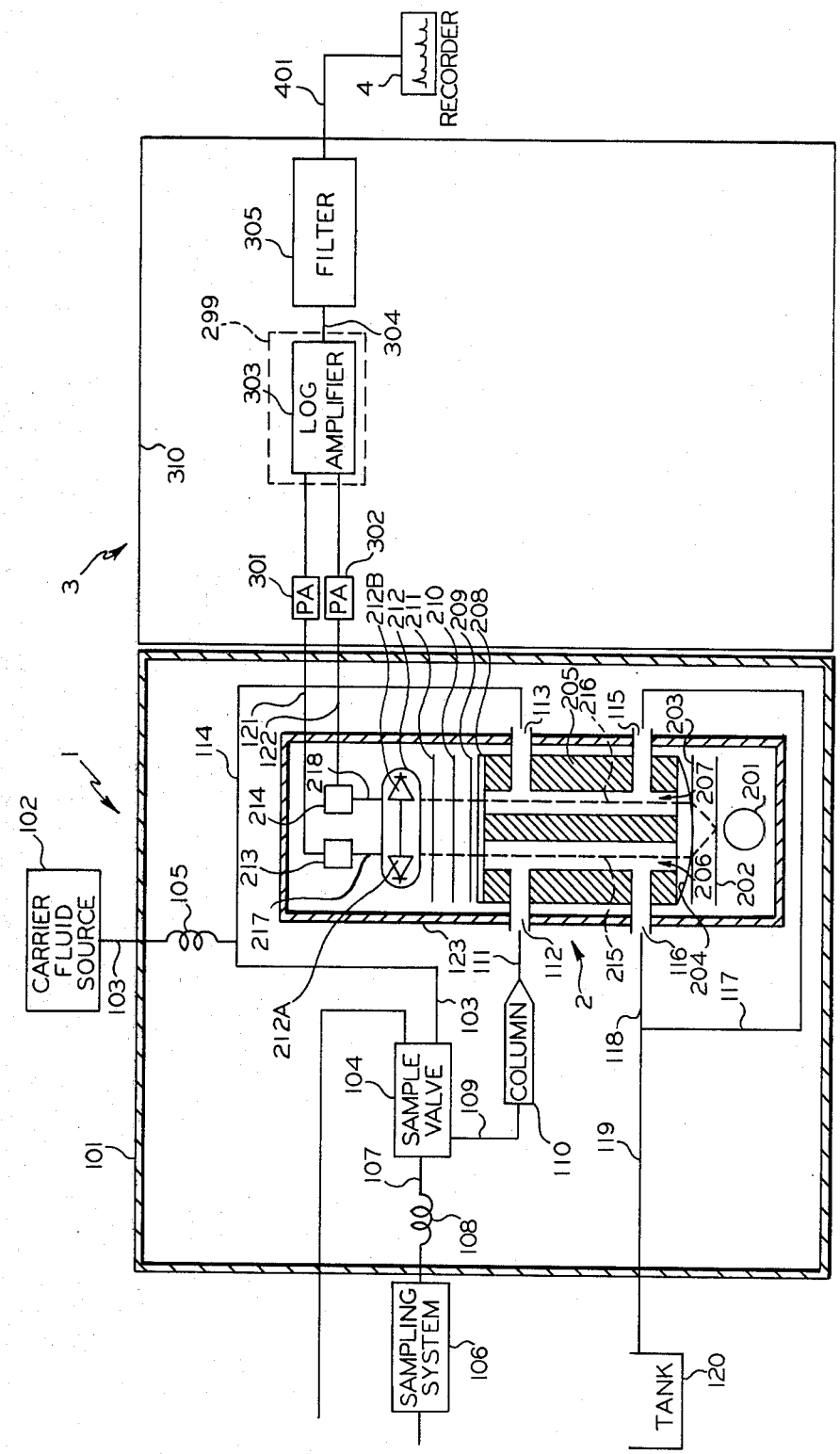
FIG. 1 is a schematic diagram of a chromatographic analyzer in accordance with one embodiment of the present invention.

As used herein, the term optically aligned means that one element for passing a beam of light is connected in light communication with another element so that at least a substantial portion of the light leaving the first element reaches the second element. When an aperture, for example, is said to be optically aligned with a light beam or an element from which or to which a light beam is passed the term means that the elements are aligned so at least a substantial portion of a light beam can pass through the aperture from or to the element or light beam.

Our invention broadly comprises an optical absorbance detector.

In one aspect, the optical absorbance detector comprises light means for producing a first light beam and a second light beam; flow cell means comprising first fluid light path means for passing a first fluid through the first light beam to produce a first light signal representative of the first fluid and second fluid light path means for passing a second fluid through the second light beam to produce a second light signal representative of the second fluid; optical means comprising geometrical optics elements for reducing refractive index error, the optical means connecting the light means in light communication with the flow cell means so that the first beam passes through the first fluid light path means and so that the second beam passes through the second fluid light path means; first detecting means optically aligned with the first light signal for detecting the first light signal and for producing a first electrical signal representative of the first light signal; and second detecting means optically aligned with the second light signal for detecting the second light signal and for producing a second electrical signal representative of the second light signal.

In another aspect, the optical absorbance detector comprises radiation point source means for producing a point source of light; first spatial filter means optically aligned with the radiation point source means and operable for producing a first light beam and a second light beam, the first spatial filter means having an opaque portion opaque to radiation from the radiation point source means, said opaque portion having a first through aperture and a second through aperture, each of the first through aperture and the second through aperture being optically aligned with the radiation point source means, the first through aperture allowing the first light beam to pass therethrough and the second through aperture allowing the second light beam to pass therethrough, the first aperture and the second aperture further being separated from one another by at least a portion of the opaque portion of the first spatial filter means; collimating means optically aligned with the first spatial filter means for collimating the first light beam to produce a first collimated light beam and for collimating the second light beam to produce a second collimated light beam; first flow cell means for passing a first fluid through a first fluid light path optically aligned with the first collimated light beam to produce a first light signal representative of the first fluid; second flow cell means for passing a second fluid through a second fluid light path optically aligned with the second parallel light beam to produce a second light signal representative of the second fluid; first detector means for producing a first electrical signal representative of the first light signal; second detector means for producing a second electrical signal representative of the second light signal; and light path means for connecting the first light signal in light path communication with the first detector means and for connecting the second light signal in light path communication with the second detector means.

In another aspect, the light path means in accordance with our invention comprises at least a second spatial filter means having an opaque portion thereof opaque to radiation from the radiation point source means, said opaque portion having a first aperture being optically aligned with the first light signal and with the first detector means, and a second aperture being optically aligned with the second light signal and with the second detector means.

In another aspect, our invention comprises a chromatographic analyzer employing an optical absorbance detector in accordance with our invention and which further comprises chromatographic means for producing a first fluid having a composition representative of a carrier fluid plus sample; reference fluid means for producing a second fluid having a composition representative of essentially only the carrier fluid; first conduit means for connecting the first fluid in flow communication with the first fluid light path; second conduit means for connecting the second fluid in flow communication with the second fluid light path; and difference signal means for receiving the first electrical signal and the second electrical signal and operable to produce a difference signal representative of the difference in composition of the first fluid and the second fluid.

In yet another aspect, our invention comprises a chromatographic analyzer suitable for process applications in which the optical absorbance detector is contained in an explosion resistant housing which is in turn contained, along with the chromatographic means, the first conduit means, and the second conduit means, in a temperature controlled oven.

In yet other aspects, our invention comprises methods for detecting optical absorbance, methods for chromatographic analysis, and methods for process chromatography.

DETAILED DESCRIPTION OF THE INVENTION

The invention is described in terms of a specific chromatographic analyzer system and a specific optical absorbance detector. The invention is, however, also applicable to other chromatographic analyzer systems and/or also applicable to other optical absorbance detectors in which the principles of the present invention can be applied by one familiar with the art.

Referring now to the drawings in detail, FIG. 1 shows generally a process chromatographic analyzer in accordance with our invention. Analyzer-detector 1 comprises chromatographic analysis means, for example, a chromatographic column and associated equipment, and further comprises the optical absorbance detector means 2 (hereinafter referred to as detector means 2). Both the chromatographic analysis means and the detector means 2 are contained in a temperature controlled oven 101. Detector means 2 is further contained in an explosion proof housing 123. Difference signal means 3 comprises electronic circuitry enclosed in a purged gas enclosure suitable for use in hazardous environments such as process plants where it can be desirable to isolate electronics and electrical equipment from such as, for example, inflammable vapors.

Analyzer-detector 1, contained within temperature controlled oven 101, is operable for separating sample components in time, for detecting the thus separated components, and for producing a first electrical signal 121 representative of the composition of a sample stream comprising sample and a carrier fluid and a second electrical signal 122 representative of the composition of a reference stream comprising essentially only carrier fluid. First electrical signal 121 and second electrical signal 122 are provided to difference signal means 3 which is operable for producing a difference signal 401 which is representative of the difference in composition between the sample stream and the reference stream. Difference signal 401 is provided to a recorder 4 such as is known in the art to produce a chromatogram representative of the difference in composition between the sample stream and the reference stream.

Oven 101 is operable for maintaining the enclosed components at a predetermined temperature compatible with process applications. The predetermined temperature can be such as, for example, a temperature in the range of about 60° F. to about 400° F. Oven 101 has a housing which can comprise an outer shell preferably of metallic construction such as of steel or aluminum construction and an inner insulating layer which can be any suitable insulating material such as, for example, fiberglass insulation. The oven temperature can be controlled by such as, for example, an on/off type controller (not shown) that utilizes a thermistor temperature sensing element operatively connected to a 1000 watt electrical heating element (not shown). Other heating elements and controls can of course also be used. Forced air circulation can be maintained in the oven. The controller means can be any suitable controller for maintaining the oven at the desired temperature.

A carrier fluid stream is introduced from a suitable carrier fluid source 102 through conduit means 103 which passes through the oven 101 enclosure into sample valve 104. Conduit means 103 includes a preheater 105 for heating the carrier fluid to oven temperature. A sample of a fluid to be analyzed is delivered from sampling system means 106 to sample valve 104 by conduit means 107 which passes through the oven 101 enclosure. Conduit means 107 includes preheater 108 which is operable for heating the sample of the fluid to be analyzed to oven temperature. A conduit means 109 extends between sample valve 104 and the inlet to a chromatographic column 110. Conduit means 111 extends between the outlet of chromatographic column 110 and a first inlet 112 of an optical absorbance detector designated generally by reference numeral 2. A second fluid comprising essentially only carrier fluid is passed through a reference portion of detector 2 by being introduced into a second inlet 113 of detector 2 through conduit means 114 which communicates with conduit means 103. Carrier fluid also flows from conduit means 103 through sample valve 104, chromatographic column 110, and conduit means 111 to the first inlet 112 of detector 2.

At the beginning of an analysis period, sample valve 104 is actuated, for example, by a programmer (not shown) to introduce a predetermined volume of sample into the carrier fluid flowing through chromatographic column 110. The constituents of the sample are separated in time and eluted in sequence and flow from the chromatographic column 110 through conduit means 111 and first inlet 112 to the sample portion of detector 2 as the first fluid.

After flowing through the detector 2 the sample stream leaves the sample portion of detector 2 by outlet 116 and the reference stream leaves the reference portion of detector 2 by outlet 115. Outlets 115 and 116 of detector 2 are connected in flow communication with conduit means 117 and 118 respectively which are removed from the oven enclosure by conduit means 119 which passes through the enclosure 101 to a waste tank 120.

Detector 2, as indicated above, establishes a first electrical signal 121 representative of the composition of the first fluid comprising carrier fluid carrying the sample passing through the sample portion of detector 2 and a second electrical signal 122 representative of the composition of essentially only the carrier fluid passing through the reference portion of detector means 2.

Figure 2:
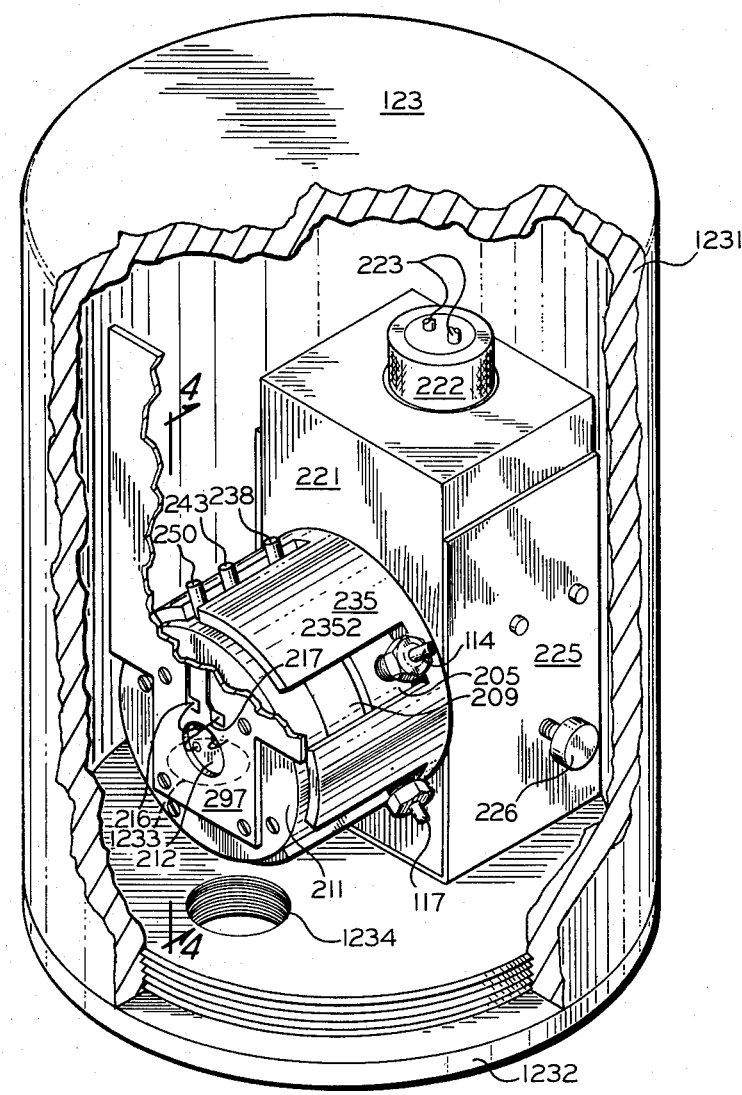
FIG. 2 is a perspective view of an optical absorbance detector in accordance with one embodiment of the present invention having the explosion resistant housing and circuit board partially broken away.

The optical absorbance detector 2 can be enclosed in an explosion resistant housing 123 which, as shown in FIG. 2, comprises a threaded basal portion 1232 having a first opening 1233 therethrough for electrical conduit means and a second opening 1234 for fluid conduit means. The explosion resistant housing further comprises a cap portion 1231 which, in the illustrated embodiment, threadably engages basal portion 1232. The housing is made of a suitable explosion resistant material such as, for example, a metal such as steel or aluminum and can have a black anodized coating to reduce stray light interference.

Referring again to FIG. 1, optical absorbance detector 2 comprises radiation source means 201 for producing light of suitable wavelengths, radiation point source means 202 for permitting only a thin beam of the thus produced light to pass therethrough, first spatial filter means 203 for producing a first light beam and a second light beam, flow cell means 205 having a first fluid light path 206 and a second fluid light path 207, a quartz window 2088, second spatial filter means 209, interference filter means 210, third spatial filter means 211, and light detector means 212. Light produced from radiation source means 201 is passed through the radiation point source means 202 as from a point source. The light from the radiation point source means diverges as from a point source and impinges on first spatial filter means 203 which allows only a first light beam and a second light beam to pass therethrough. First light beam is collimated by collimating means 204 to produce a first collimated light beam 215. Second light beam is collimated by collimating means 204 to produce a second collimated light beam 216. The first collimated light beam passes through first fluid light path 206 of flow cell 205 which is in flow communication between inlet 112 and outlet 116 through which a first fluid comprising carrier fluid plus sample constituents can flow. The second collimated light beam passes through second fluid light path 207 of flow cell 205 which is in flow communication between inlet 113 and outlet 115 through which a second fluid comprising essentially only carrier fluid can flow. A portion of the first collimated light beam passing through first fluid light path 206 can be absorbed by the first fluid and the nonabsorbed light passing through forms a first light signal representative of the composition of the first fluid flowing through first fluid flow path 206. A portion of the second collimated light beam passing through the second fluid light path 207 can be absorbed by the second fluid and the nonabsorbed light passing through forms the second light signal representative of the composition of the second fluid. The first light signal and the second light signal then pass through window 2088 which is optically transparent to the wavelengths emitted by radiation source means 201. At least a portion of the first light signal then passes through spatial filter means 209, interference filter means 210, and spatial filter means 211 to impinge upon a first detector means portion 212A of light detector means 212. At least a portion of the second light signal also passes through spatial filter means 209, interference filter means 210, and spatial filter means 211 to impinge upon second detector means portion 212B of light detector means 212. The first detector means portion 212A is operable for producing an electrical signal 217 representative of the first light signal. The second detector means portion 212B is operable for producing an electrical signal 218 representative of the second light signal. Electrical signal 217 is amplified by preamplifier 213 to produce a first output signal 121 representative of the composition of the first fluid. Electrical signal 218 is amplified by preamplifier 214 to produce a second output signal 122 representative of the composition of the second fluid.

First electrical output signal 121 and second electrical output signal 122 are provided to difference means 3 which can be preferably contained in a purged enclosure 310. Preferably, the air is purged from enclosure 310 by an inert gas such as, for example, nitrogen or the like.

First electrical output signal 121 is provided to preamplifier 301 to produce an amplified first electrical signal which is provided to a first input of logarithmic amplifier means 303. Second electrical output signal 122 is provided to preamplifier 302 to produce an amplified second electrical signal which is provided to a second input of logarithmic amplifier means 303. Logarithmic amplifier means 303 is operable for producing an output function signal 304 which is representative of the logarithm of the ratio of the amplified first electrical signal to the amplified second electrical signal, and therefore representative of the difference in composition between the first fluid and the second fluid. Logarithm amplifier 303 can be temperature stabilized by a card oven 299 schematically shown in dashed lines.

Output signal 304 is provided to filter means 305 which is operable for removing undesired noise from the signal and producing difference signal 401 which is a filtered output signal representative of the difference in composition between the first fluid and the second fluid. Difference signal 401 is provided to a recorder 4 operable for producing a chromatogram representative of the difference in composition between the first fluid and the second fluid.

One preferred embodiment of the optical absorbance detector according to our invention is illustrated in more detail in FIG. 2, FIG. 3, FIG. 4, FIG. 5, and FIG. 9.

As shown in FIG. 2, block 221 can be mounted to the basal portion 1232 of explosion proof housing 123 by a bracket 225. Other components of the optical absorbance detector 2 can be supported by block 221 as described in more detail below.

Radiation source 201 can be any suitable radiation source of light for optical spectroscopy. The lamp can be a broad emission source such as hydrogen or deuterium discharge lamps, tungsten lamps, and tungsten-iodine lamps. More preferably the radiation source 201 is a discrete line emission source such as gas discharge lamps with narrow lines of emission. The gas discharge lamp can be such as, for example, mercury, zinc, and cadmium lamps. Exemplary lamps which can be used are shown in Table I.

TABLE I

| Emission Source | Model | Source |
| --- | --- | --- |
| Zinc | Z-800 | Ultra-Violet Products, Inc. San Gabriel, CA |
| Mercury | Pen-Ray 9-0033-01 | San Gabriel, CA |
| Cadmium | CD-480 | Ultra-Violet Products, Inc. San Gabriel, CA |

Radiation source 201 is preferably mounted in block 221. Block 221 comprises a first opening 233 opening on a first surface of block 221, which communicates with a first chamber 228 for insertably receiving radiation source 201. Preferably the radiation source 201 is placed in close proximity to the block 221 to allow good thermal exchange within chromatograph oven 101 thereby facilitating maintenance of thermal equilibrium. O-rings 2281 and 2282 can provide a resilient seating for the radiation source 201 and/or shield 227 as described below. Because various of the lamps suitable for optical spectroscopy can be of various sizes, optionally a shield 227 can be employed to insure good thermal exchange. Shield 227 can be a generally cylindrical shield having alignment aperture 229 and emission aperture 224 to allow light to pass therethrough into the light path as herein described. Alignment aperture 229 can be used to align the emission aperture 224 with block emission aperture 208 and the shield or lamp can then be locked in place by set screw 226 as shown in FIG. 2 which passes through the block 221.

Block 221 can further comprise a chamber 230 opening onto a second surface of block 221. Chamber 230 can have a first outer generally cylindrical portion 2302 for receiving a portion of alignment holder 235 as hereinafter described, a second generally cylindrical portion 2301 having a diameter preferably smaller than that of first portion 2302, and an inner inwardly converging frustoconical portion 2303. Emission aperture 202 can connect the lamp 201 in light communication with the apex of frustoconical portion 2303 of chamber 230 so that light passes therethroug as from a point source.

Chamber 230 can be included to decrease interference effects which can otherwise arise from internal reflection on the sidewalls of emission aperture 208. Chamber 230 can be especially useful in decreasing such effects when a radiation source emitting in the visible range is employed.

Aperture means are provided for allowing only a small amount of light from source means 201 to pass therethrough. Emission aperture 202 allows light from radiation source 201 to pass therethrough and the combination of emission aperture 202 and the radiation source means 201 can therefore act as radiation point source means for emitting light as from a point source to secure the advantages hereinafter described.

"Point source" as used herein means a source of light of very small size, i.e., small with respect to the distance away (in this case the distance to the collimating means 204 as discussed below),, so that the angular subtense is very small. While geometrical optics would make the image of the point source a point, actually the image is a diffraction pattern of finite dimensions. The diffraction pattern arises from interference of waves propagating in different directions. Nevertheless as aperture size decreases, light passing through the aperture acts increasingly like a point source from which waves progress substantially only radially generating a spherical wavefront.

The light passing through emission aperture 202 propagates substantially radially outwardly to first spatial filter means 203. First spatial filter means 203 comprises an opaque portion opaque to radiation from the radiation source, said opaque portion having a first aperture 2031 and a second aperture 2032 passing therethrough, the first aperture 2031 permitting a first beam of radiation from the emission aperture 202 to pass therethrough and the second aperture 2032 permitting a second beam of radiation from the emission aperture 202 to pass therethrough. Preferably each of first aperture 2031 and second aperture 2032 are generally parallel to one another so that the longitudinal axis of the first light beam is generally parallel to the longitudinal axis of the second light beam. First aperture 2031 and second aperture 2032 can each have a light-proximal flared portion flaring outwardly toward the light source and a light distal generally cylindrical portion. Spatial filter means 203 can have a light distal generally concave portion or cup 2033 for receiving and at least partially supporting a respective portion of the collimating means 204 and for urging engagement of a planar surface of the collimating means with flow cell 205 to form a fluid seal as described below.

Collimating means 204 can preferably comprise a planoconvex collimating lens having a generally convex light proximal surface 204B and a generally planar light distal surface 204A. The collimating means 204 is operable for collimating the first light beam to produce a first collimated light beam and for collimating the second light beam to produce a second collimated light beam. Preferably the collimating lens has a focal length generally equal to the distance between the center of the collimating lens and the emission aperture 202. The generally convex light proximal surface 204B can be received and at least partially supported by generally convex cup 2033. The generally planar surface 204A can be urged against flow cell 205 to form a fluid seal as described in more detail below.

Collimating lens 204 is any suitable collimating lens for making each of the first light beam and the second light beam from the second spatial filter follow a generally parallel path in contradistinction to the usually diverging path followed by a beam of light so that the light passing through first light flow path 206 and second light flow path 207 is substantially parallel to the sides of the respective flow paths inside flow cell 205. Preferably the collimating lens has a focal distance equal to the distance between emission aperture 202 and the center of collimating lens 204. The collimating lens is preferably made of a material which substantially passes light of visible and/or ultraviolet wavelengths. For example, the collimating lens can be ground from a material such as S1-UV grade quartz available from Esco Products, 171 Oakridge Road, Oakridge, N.J. A collimating lens having a specified focal distance and made from such an ultraviolet-transparent material can be ordered from a commercial supplier, such as Esco Products, 171 Oakridge Road, Oakridge, N.J.

The combination of radiation point source means, first spatial filter means, and collimating means as herein described produces a first collimated light beam 215 and a second collimated light beam which enters the flow cell at an angle generally perpendicular to the interface between the flow cell and generally planar surface 204A of collimating means 204. The combination is effective to minimize refractive index effects which can arise from light beam components which do not impinge perpendicularly on the interface between the fluid in the respective fluid light paths and the ambient environment.

Thus, the combination of radiation point source means, first spatial filter means, and collimating means comprises refractive index correcting optics. In the preferred embodiment described herein, the refractive index correcting optics comprise elements of geometrical optics. The combination can reduce error arising from refractive index effects which can arise when light components do not enter the fluid-ambient interface perpendicularly by minimizing those nonperpendicular components. Light components which enter perpendicularly to the interface are not refracted and consequently cannot contribute to refractive index error. In addition, error arising from signal loss due to reflection at the interface is minimized. This means of minimizing refractive index error can be effective whatever the source of the refractive index error.

The diameter of emission aperture 202 is preferably as small as possible to produce a radiation point source means for producing a light beam which acts like a point source from which waves progress substantially only radially producing a generally spherical wavefront. The lower limit of aperture size is determined by the radiation source, optics, and electronics of the entire system because the light passing through the emission aperture 202 must have sufficient intensity for detection by detection means 212. In the illustrated embodiment, the diameter of aperture 202 can be at least 0.030 inches, preferably in the range from about 0.050 to about 0.070 inches, more preferably in the range of about 0.058 to about 0.065 inches.

Preferably each of the first aperture 2031 and the second aperture 2032 of the first spatial filter means 203 has a diameter at least effective to allow sufficient light to pass therethrough to be respectively detected by the first detector means and the second detector means. The diameter of each of the generally cylindrical portions of first aperture 2031 and second aperture 2032 is preferably at the separation distance separating first aperture 2031 and second aperture 2032 less than the diameter at which greater than 1% crossover of light or light crosstalk between the first light beam and the second light beam can occur. More preferably, the diameter is such that essentially zero crossover occurs. As stated, however, the diameter of first aperture 2031 and second aperture 2032 must be sufficiently large to pass an amount of light effective for detection by detection means 212. In the illustrated embodiment, the diameter of first aperture 2031 and of second aperture 2032 can be broadly in the range of about 0.025 to about 0.045 inches, preferably in the range of about 0.029 to about 0.036 inches, more preferably in the range from about 0.031 to about 0.034 inches. Aperture 2031 can be separated from aperture 2032 by a distance measured between the center of aperture 2031 and the center of aperture 2032 of at least 0.15 inches to about 0.180, more preferably in the range of about 0.160 to about 0.170 inches. The apertures are separated by a separation distance such that at the particular aperture diameter utilized crosstalk or crossover between the first light beam and the second light beam is minimized. Such cross over can result when the path length is sufficient to allow the diverging light beams from aperture 2031 and 2032 to overlap or interfere with each other. Such overlap is especially harmful to linearity of function at the upper end of an absorption range or a lower end of a transmission range where only a small amount of light passes through a sample because relatively small amounts of light crossover from the relatively much stronger reference beam can then significantly affect the sample reading.

First spatial filter means 203 preferably comprises a portion of a combined collimator lens holder and optical alignment means 235, hereinafter referred to as alignment holder 235. Alignment holder has a generally discoidal base 2351 and a generally cylindrical sidewall 2352 shown in FIG. 2 and FIG. 3.

Sidewall 2352 is interrupted by an alignment slot 236 for receiving the alignment pins 238, 243, and 250 thereby to align apertures contained in each of means 205, 209, and 211 for in light communication. Sidewall 2352 can also be interrupted by a plurality of slots 237 for permitting access to flow cell 205 for attachment of conduit means as illustrated in FIG. 2.

Discoidal base 2351 has a central portion thereof comprising the first spatial filter means 203 as hereinabove described. Discoidal base 2351 can have a light proximal surface having an alignment ring 2353 which can be insertably received in first outer cylindrical portion 2302 of chamber 230 in block 221. Discoidal base 2351 can further have an alignment hole 2354 in the light proximal surface which mates with an alignment pin 231 on block 221 to facilitate rapid alignment of the optical system of detector 2. The alignment holder 235 can be attached to block 221 by suitable fasteners such as bolts 248 which threadably engage tapped holes 2321 or 2322.

Flow cell 205 in the illustrated embodiment is generally cylindroid in shape having two generally planar surfaces 205A and 205B and having openings and passages therein as described below. Preferably the length of the flow cell along its longitudinal axis is 1 centimeter so that the first fluid path and the second fluid light path as described below are also 1 centimeter in length. This dimension is chosen for ease and convenience since absorption and transmission of light are easily computed using 1 centimeter light paths, however, the flow path can have any suitable length.

As indicated, flow cell 205 has therein a first fluid light path 206 and a second fluid light path 207 passing through the flow cell from a first generally planar surface 205A to a second generally planar surface 205B of flow cell 205. Each of first fluid flow path 206 and second fluid flow path 207 are generally parallel to a longitudinal axis of flow cell 205 and are optically aligned with the first collimated light beam and the second collimated light beam respectively to thereby form a first fluid light flow path through which the first collimated beam passes and a second fluid light flow path through which the second collimated beam passes respectively. First fluid light flow path 206 communicates on a first generally planar surface 205A of flow cell 205 with a first groove 240A and on a second generally planar surface 205B of flow cell 205 with a second groove 240B. Second fluid flow path 207 communicates on the first generally planar surface of flow cell 205 with a third groove 241A and on the second generally planar surface 205B with a fourth groove 241B.

The diameter of the first fluid flow path and the second fluid flow path is chosen so that the volume of the flow path is small to assure high sensitivity. For a 1 centimeter flow path in accordance with the illustrated embodiment, each of the first fluid light path 206 and the second fluid light path 207 can have a diameter broadly in the range of about 0.03 to about 0.08 inches, more preferably in the range from about 0.045 to about 0.065 inches, most preferably in the range from about 0.055 to about 0.065 inches.

As best seen in FIG. 9 the flow cell further has a first fluid inlet 112 which is in flow communication via conduit means 1121 with the first groove 240A; and second groove 240B is in flow communication via conduit means 1124 with first fluid outlet 116. Second fluid inlet 113 communicates with groove 241B via conduit means 1131; and groove 241A is in flow communication with second fluid outlet 115 via conduit means 1151.

Surface 205A has a groove 242A and surface 205B has a groove 242B. Groove 242B has an outside diameter slightly greater than the diameter of the collimating lens 204 to facilitate a fluid seal between the generally planar surface 204A of collimating lens 204 and the portion of surface 205B which comprises grooves 240B and 241B. Groove 242A has an outside diameter slightly greater than the diameter of quartz window 2088, described below, to facilitate a fluid seal between quartz window 2088 and the portion of flow cell surface 205A which comprises grooves 240A and 241A. Preferably the flow cell is made of resilient material such as, for example, Tefzel ® to enhance the fluid seals. Tefzel ® is available from Bunnell Plastics, Inc., Middleton, N.J. 08056.

Thus a first flow path is defined whereby a first fluid can flow into first inlet 112 through conduit means 1121 to groove 240A, thence through light flow path 206 in which flow path the sample fluid can absorb light from the first collimated light beam, thence along groove 240B and conduit 1124 to outlet 116. A second flow path is similarly defined whereby a second fluid can flow into inlet 113 through conduit means 1131 to groove 241B, thence through second fluid light flow path 207 in which flow path the second fluid can absorb light from the second collimated light beam, thence along groove 241A and conduit 1151 to outlet 115. As indicated above, flow paths 206 and 207 preferably have a 1 centimeter path length so that light is absorbed by the respective fluid therein over that distance.

Window means 2088 can be any suitable window which substantially allows wavelengths of interest to pass. Preferably, the window can be made of an ultraviolet-transparent material such as S1-UV Grade Quartz available from Esco Products, 171 Oakridge Road, Oakridge, N.J.

Figure 3:
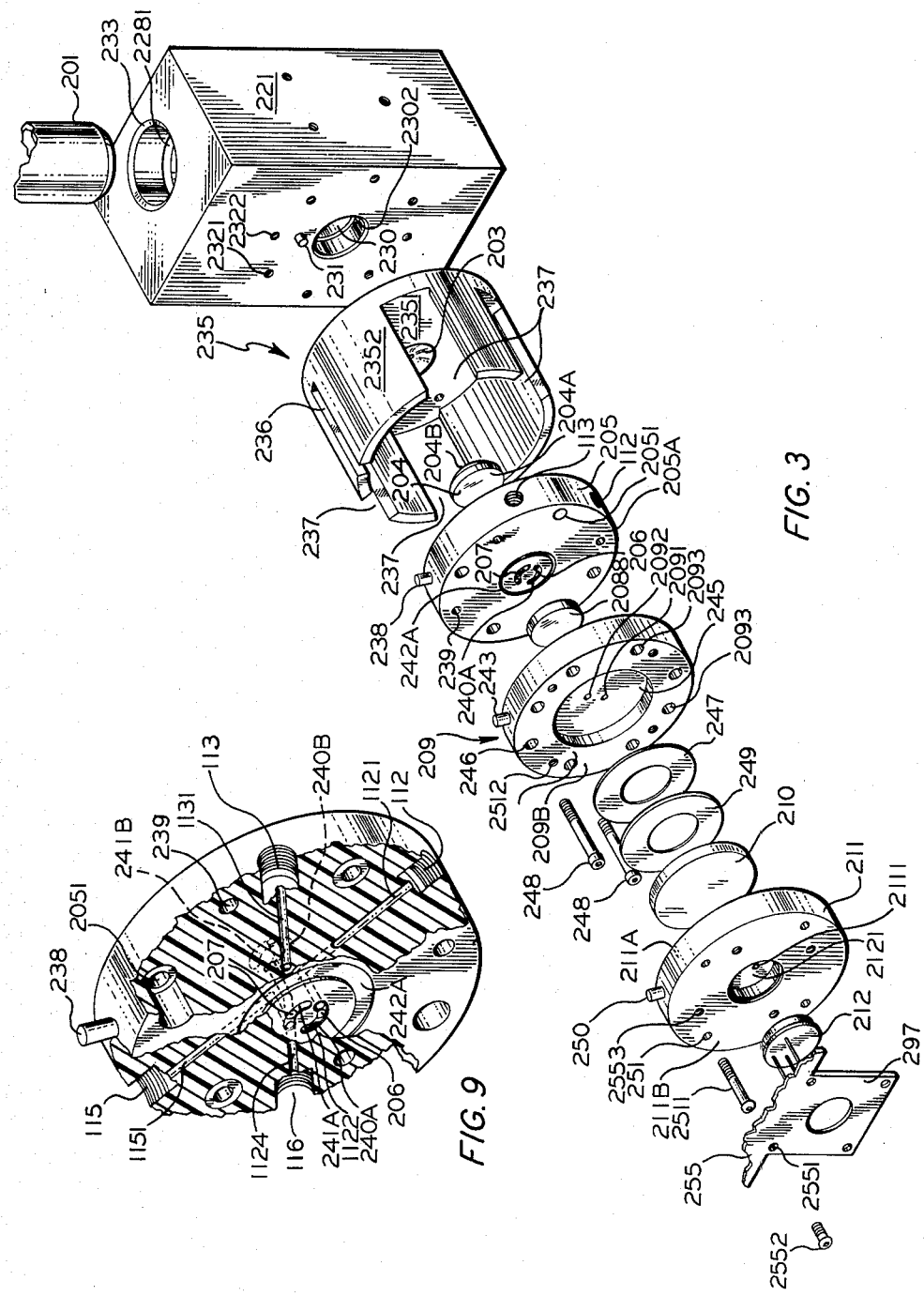
FIG. 3 is an exploded view of the optics of the optical absorbance detector of FIG. 2.
Figure 4:
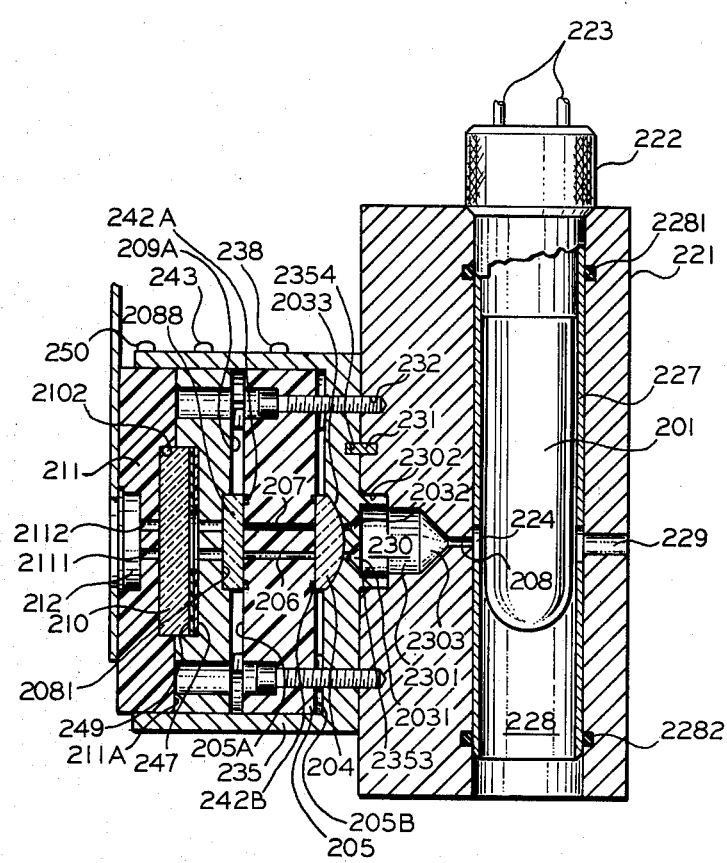
FIG. 4 is a sectional view taken along line 4—4 of FIG. 2.

Second spatial filter 209 is generally cylindroid in shape having a first side 209A and a second side 209B indicated in FIG. 3 and/or FIG. 4. Second spatial filter 209 has an opaque portion opaque to radiation from the light source. Second spatial filter 209 preferably has an outer portion having a plurality of through passages 246 and 2093 therein through which fasteners such as, for example, bolts 248 can pass to attach the filter assembly to block 221 at, for example, tapped holes 2321 and 2322. First side 209A has a generally cylindrical chamber 2081 therein to receive and support at least a portion of generally cylindrical quartz window 2088. Second side 209B has a generally cylindrical chamber 245 therein, best seen in FIG. 3, to receive and support spacers 247 and 249 and at least a portion of interference filter 210. The opaque portion of spatial filter 209 has first aperture 2091 and second aperture 2092 passing therethrough in optical alignment with flow paths 206 and 207 respectively and in further alignment with apertures 2031 and 2032 respectively so that the first light signal and the second light signal can pass therethrough. Apertures 2091 and 2092 can have a diameter slightly larger than respective apertures 2031 and 2032 to avoid signal loss. Each of apertures 2091 and 2092 can have, in the illustrated embodiment, a diameter in the range of about 0.060 to about 0.10 inches, more preferably in the range from about 0.08 to about 0.09 inches. Apertures 2091 and 2092 are separated by a distance which blocks passage of light therebetween to minimize light crossover or cross talk between the first light signal and the second light signal.

Interference filter means 210 are provided for passing only a preselected band of wavelengths therethrough connected in light path communication with the second spatial filter so that the portion of the first light signal passing through the first aperture and the portion of the second light signal passing through the second aperture are filtered through the interference filter means to remove undesired wavelengths.

Interference filter means 210 can be any suitable filter for passing a selected band of wavelengths. Preferably, interference filter 210 is an interference filter which passes only a narrow band of wavelengths which includes wavelengths at which a sample component of interest absorbs light. Suitable filters and corresponding wavelengths are shown in Table II.

TABLE II

| Filter | Model No. | Wavelengths Transmitted | Available from: |
|---|---|---|---|
| Zn | 214B | $\lambda_o = 210$ nm $\Delta\lambda = 450$ nm | Acton Research Corp., Acton, Mass. |
| Cd | 230B | $\lambda_o = 230$ nm $\Delta\lambda = 450$ nm | Acton Research Corp., Acton, Mass. |
| Hg | 254B | $\lambda_o = 250$ nm $\Delta\lambda = 500$ nm | Acton Research Corp., Acton, Mass. |

In accordance with the present invention, means are provided whereby filter 210 can be easily interchangeable. Basically, these means comprise alignment means whereby the filters can easily be removed and interchanged and fastening means for removing and interchanging interference filter 210 without interrupting flow through flow cell 205.

Third spatial filter means 211 can also be provided for further reducing stray light effects or light crossover between the first light signal and the second light signal. Third spatial filter means can have an opaque portion opaque to radiation from the radiation point source and having a first aperture and a second aperture passing therethrough, each aperture allowing at least a portion of the respective light signal passing through the interference filter to pass therethrough. Third spatial filter 211 is generally cylindroid in shape having a first side 211A and a second side 211B. First side 211A has a generally cylindrical chamber 2102 therein which can receive and support at least a portion of interference filter 210. Second side 211B has a generally cylindrical chamber or cup 2121 therein which can receive and support at least a portion of detector means 212. Spatial filter 211 further has a first aperture 2111 and a second aperture 2112 passing therethrough in optical alignment respectively with apertures 2091 and 2092 of second spatial filter 209, further in coaxial optical alignment respectively with light flow paths 206 and 207, and further in coaxial optical alignment respectively with apertures 2031 and 2032. In the illustrated embodiment, the apertures 2111 and 2112 can have a diameter in the range of about 0.08 to about 0.10 inches, more preferably in the range from about 0.090 to about 0.095 inches. Spatial filter 211 further has a plurality of apertures 251 passing therethrough through which a respective plurality of bolts 2511 can pass to attach the filter 211 to respective tapped holes 2512 in third spatial filter 209 so that the interference filter can be interchanged without interrupting flow through flow cell 205. In the preferred embodiment as illustrated in FIGS. 1 through 9 the components of the optical light path are formed so that essentially the only portion of the optical light path in which light crossover or crosstalk can occur is within such elements as collimating means 204, window 2088, interference filter 210, and the like. As best illustrated n FIG. 4, this is accomplished by having the respective portion of the holders of those elements substantially conform to the respective received and or supported portion of the elements. Thus, cup 2033 substantially conforms to the portion of collimating means 204 which is received and supported by cup 2033. Generally cylindrical chamber 2081 of holder filter 209 substantially conforms to the portion of window 2088 which is received and supported by chamber 2081. Generally cylindrical chamber 245 of holder filter 209 substantially conforms to the respective portions of O rings 247 and 249 and of interference filter means 210 which is received and supported by chamber 2101. Generally cylindrical chamber 2102 of holder filter 211 substantially conforms to the respective portion of interference filter 210 which is received and supported by chamber 2101. Generally cylindrical chamber 245 of holder filter 209 substantially conforms to the portion of detector means 212 whih is received and supported thereby. By this means, light crossover or crosstalk between light beams or signals is minimal; and, at the same time, nonuniformities which can arise from using separate lenses, windows, and the like are avoided.

Light detector 212 can be any suitable light detector for transducing a light signal to an electrical signal. Preferably, the light detector 212 is a dual silicon photodiode, Model UV 100B Dual Photodiode, available from EG & G, Electro Optics Division, 35 Congress Street, Salem, Mass., 01970. The dual silicon photidiode is presently most preferred because, since both photodiodes are formed on the same substrate, error between the two arising from thermal nonuniformities can be minimized. Alternatively, two individual photodiodes can be used, for example, such as two UV 100B Photodiodes, available from EG & G, Electro Optics Division, 35 Congress Street, Salem, Mass., 01970. The dual photodiode can also be obtained from Applied Automation, Inc., Bartlesville, Okla. 74004. The detector means 212 is preferably mounted on a preamplifier board 297 such as is known in the art and which can be mounted on filter holder 211 by a plurality of screws 2552 passing through openings 2551 in board 297 into tapped holes 2553 in holder filter 211.

Figure 5:
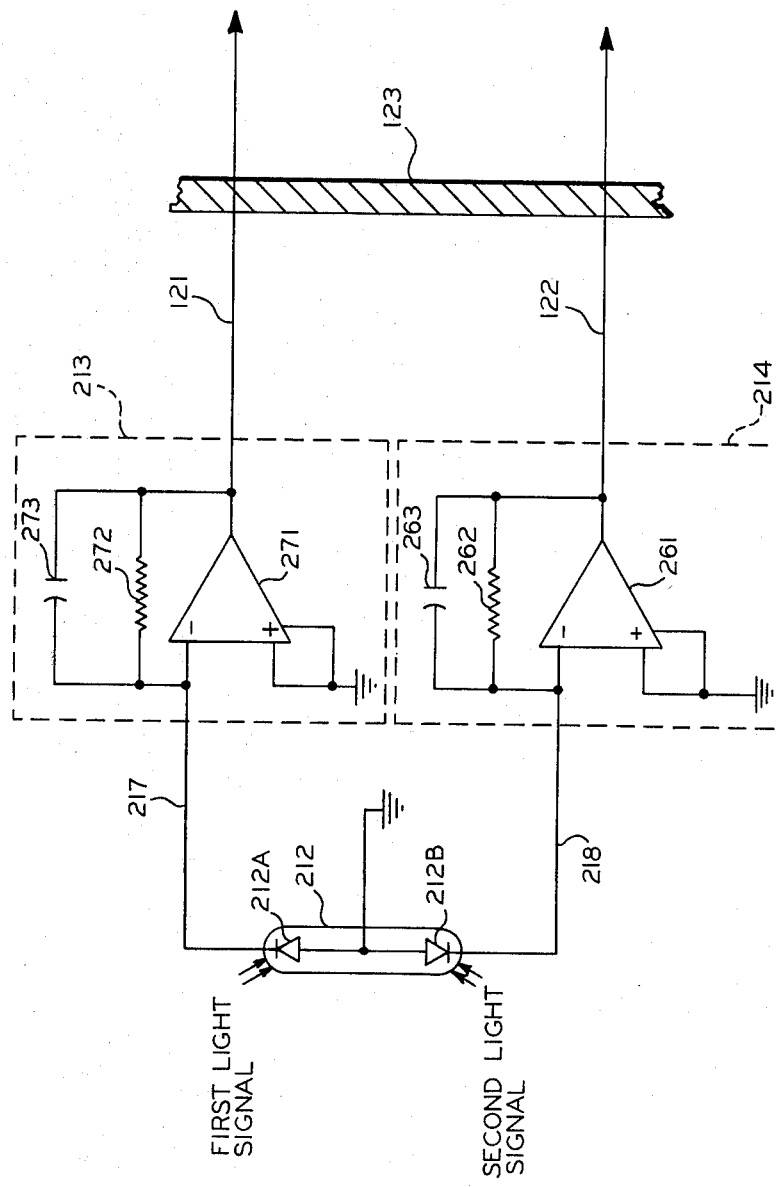
FIG. 5 is a schematic drawing of the electronics of a preamplifier board in accordance with one embodiment of the present invention.

The dual silicon photodiode 212 is located so that the light passing through light flow path 206 will fall on a first detector photodiode 212A and the light passing through second flow path 207 will fall on a second detector photodiode 212B as schematically illustrated in FIG. 5. The intensity of the light of a particular wavelength which strikes the silicon photidiodes 212A and 212B can provide an indication of the relative absorption of light by the first fluid, for example, carrier fluid plus sample flowing through light flow path 206 and the relative absorption of light by the second fluid, for example, carrier fluid flowing through reference light flow path 207. Photodiode 212A will produce an electrical signal 217 representative of the intensity of the light passing through the first fluid light flow path 206, i.e., representative of the first light signal. Photodiode 212B can provide an electrical signal 218 representative of the intensity of light passing through the second fluid light flow path 207, i.e., representative of the second light signal and can be mounted on preamplifier board 297.

Signal 217 is provided from the cathode side of silicon photodiode portion 212A to a preamplifier 213; and signal 217 is provided from the cathode side of silicon photodiode portion 212B to a preamplifier 214. Preamplifiers 213 and 214 are shown schematically in FIG. 5.

Signal 217 is provided from the cathode side of silicon photodiode 212A to the inverting input of operational amplifier 271. The noninverting input of operational amplifier 271 is tied to ground. The output of operational amplifier 271 is fed back to the inverting input of the operational amplifier 271 through the parallel combination of resistor 272 and capacitor 273. The output of operational amplifier 213 also provides output signal 121 which is provided to preamplifier 301, discussed below. Operational amplifier 271 provides amplification for signal 217 which will be a very small current, typicaly in the nanoamp range.

In like manner, signal 218 is provided from the cathode side of silicon photodiode 212B to the inverting input of operational amplifier 261. The noninverting input of operational amplifier 261 is tied to ground. The output of operational amplifier 261 is fed back to the inverting input of the operational amplifier 261 through the parallel combination of resistor 262 and capacitor 263. The output of operational amplifier 261 also provides output signal 122 which is provided to preamplifier 302 as discussed below. Operational amplifier 261 provides amplification for signal 218 which will also be a very small current, typically in the nanoamp range.

The output signals 121 and 122 are fed from the explosion proof housing 123, thence through oven housing 101, thence through purged enclosure housing 310 which provides a purged enclosure for the difference signal means 3 electronics, best seen in FIG. 1.

Figure 6:
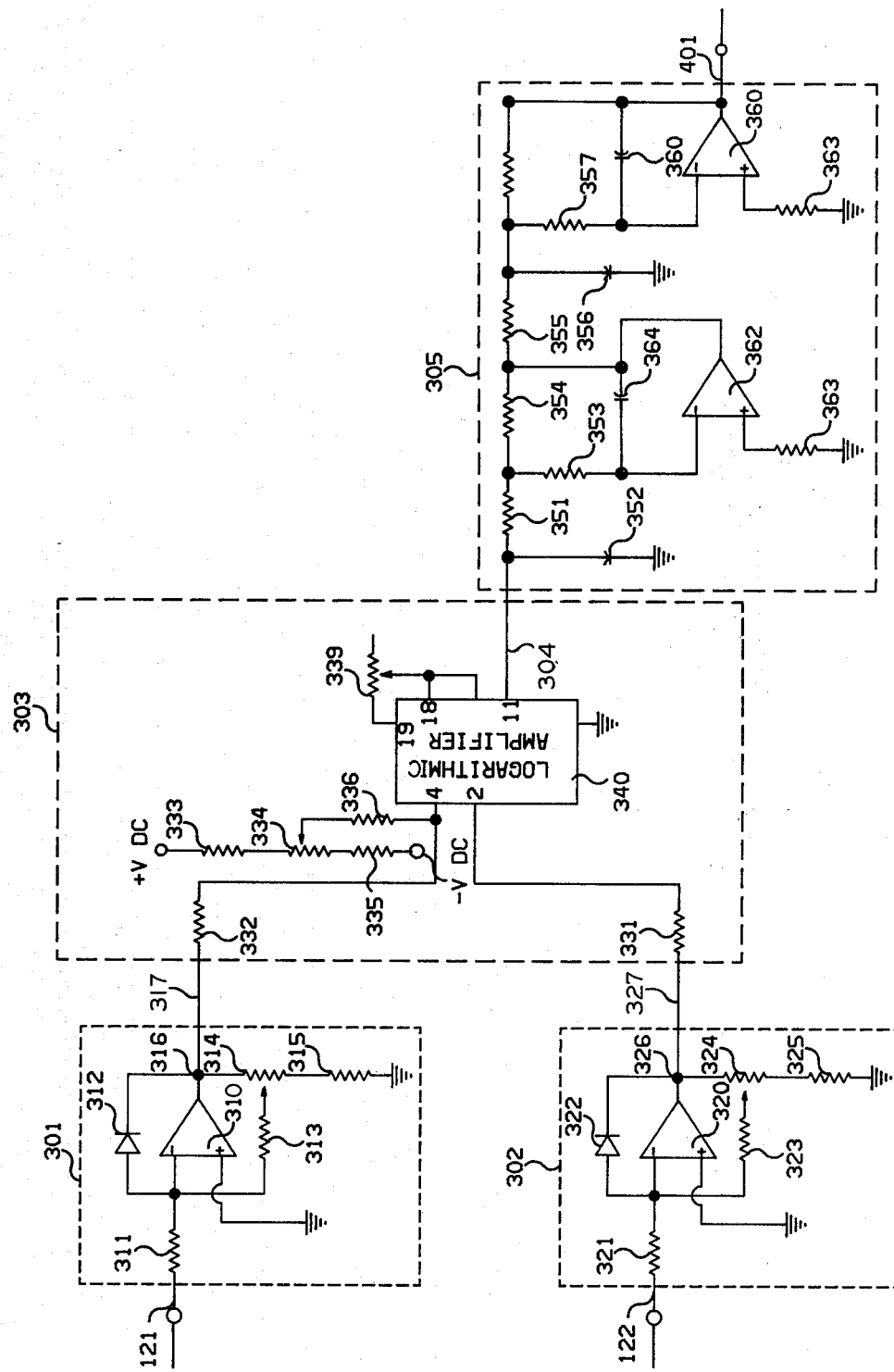
FIG. 6 is a schematic drawing of the analyzer-detector electronics in accordance with one embodiment of the present invention.

Referring now to FIG. 6, output signal 121, which is representative of the light passing through the first fluid light path 206, is provided as an input to preamplifier 301. Output signal 121 is tied to the inverting input of operational amplifier 310. The noninverting input of operational amplifier 310 is tied to ground. The output of operational amplifier 310 is fed back to the inverting input of operational amplifier 310 via diode 312. The output from the operational amplifier 310 is also tied to one terminal of potentiometer 314. A second terminal of potentiometer 314 is tied to ground through resistor 315. The wiper of potentiometer 314 is tied to the inverting input of operational amplifier 310 through resistor 313. Operational amplifier 310 and potentiometer 314 provide a means by which the gain of the first electrical signal output 121 from the detector 2 can be varied. The setting of the potentiometer 314 determines the signal level which appears at node 316 and therefore the level of output signal 317.

Output signal 122, which is representative of the light passing through second fluid light path 207, is provided as an input to preamplifier 302. Output signal 122 is tied to the inverting input of operational amplifier 320. The noninverting input of operational amplifier 320 is tied to ground. The output of operational amplifier 320 is fed back to the inverting input of operational amplifier 320 via diode 322. The output from the operational amplifier 320 is also tied to one terminal of potentiometer 324. A second terminal of potentiometer 324 is tied to ground through resistor 325. The wiper of potentiometer 324 is tied to the inverting input of operational amplifier 320 through resistor 323. Operational amplifier 320 and potentiometer 324 provide a means by which the gain of reference output 122 from the detector 2 can be varied. The setting of the potentiometer 324 determines the signal level which appears at node 326 and therefore the level of output signal 327.

The output signal 317 from preamplifier 301 is provided as a first input to the logarithmic amplifier 340 through resistor 332. The output signal 327 from preamplifier 302 is provided as a second input to the logarithmic amplifier 340 through resistor 331. The logarithmic amplifier 340 is preferably a 4127 KG manufactured by Burr-Brown. The logarithmic amplifier 340 provides an output function signal 304 which is substantially equal to the logarithm of the ratio of the voltage level of output signal 317 from operational amplifier 310 to the voltage level of output signal 327 from operational amplifier 302, i.e., to logarithm. Signal 304, which is representative of the relative amount of light absorbed by the first fluid passing through first fluid light path 206 relative to the amount of light absorbed by the second fluid flowing through the second fluid light path 207, is provided as an input to filter 305.

In the illustrated preferred embodiment, the output signal 317 is provided to the sample input pin 4 of a 4127 KG manufactured by Burr Brown. The output signal 327 is provided to the reference input pin 2. External rheostat 339 sets the current level of the input signal at pin 2 and acts as a gain control. A wiper of potentiometer 334 is tied to input pin 4 through a resistor 336. The potentiometer 334 has a first terminal tied to a positive DC voltage source, for example, +12 volts DC, through resistor 333, and has a second terminal tied to a negative DC voltage source, for example −12 volts DC through resistor 335. Potentiometer 334 acts as an offset gain adjust control for logarithmic amplifier 340.

Filter 305 is an active filter capable of removing unwanted noise from the signal 304 and has a cutoff frequency of about ⅛ Hertz. Filter 305 is a low pass filter for removing noise components having a frequency of about ⅛ Hertz or greater from signal 304. Output signal 304 is tied to a first lead of capacitor 352 which has a second lead tied to ground. The first lead of capacitor 352 is also tied to the inverting input of operational amplifier 362 through resistor 351 and resistor 353. The noninverting input of operational amplifier 362 is tied to ground through resistor 363. The output of operational amplifier 362 is tied back to the inverting input of operational amplifier 362 through resistor 354 and resistor 353, both of which are in series combination parallel with capacitor 364. The output of operational amplifier 362 is also tied to the inverting input of operational amplifier 360 through resistor 355 and resistor 357. The common tie point of resistor 355 and resistor 357 is tied to ground through capacitor 356. The noninverting input of operational amplifier 360 is tied to ground through resistor 361. The output of operational amplifier 360 is tied back to the noninverting input of operational amplifier 360 through resistor 358 and resistor 357 which are connected in series. Capacitor 359 is also tied between the output of operational amplifier 360 and the noninverting input of operational amplifier 360. The output of operational amplifier 360 also provides output signal 401 which is provided to recorder 4 as shown in FIG. 1. The low pass filter 305 can give improved noise rejection improving signal to noise ratio.

In a further aspect as indicated above, the invention comprises temperature stabilized electronics for difference means 3. Generally this can be accomplished by selecting components which are temperature stable over the range of operating temperatures encountered by the electronics. However, in the case of the logarithmic amplifier suitable wide range stability could not be obtained by such means. The solution was to enclose the logarithmic amplifier in a card oven mounted on the printed circuit board carrying the logarithmic amplifier. The small card oven mounted over the logarithmic amplifier maintains a constant temperature for that component. The card oven for a circuit board according to our invention comprises enclosure means attached to the circuit board for enclosing circuit components to be temperature stabilized and temperature control means for controlling the temperature in the enclosure.

Figure 7:
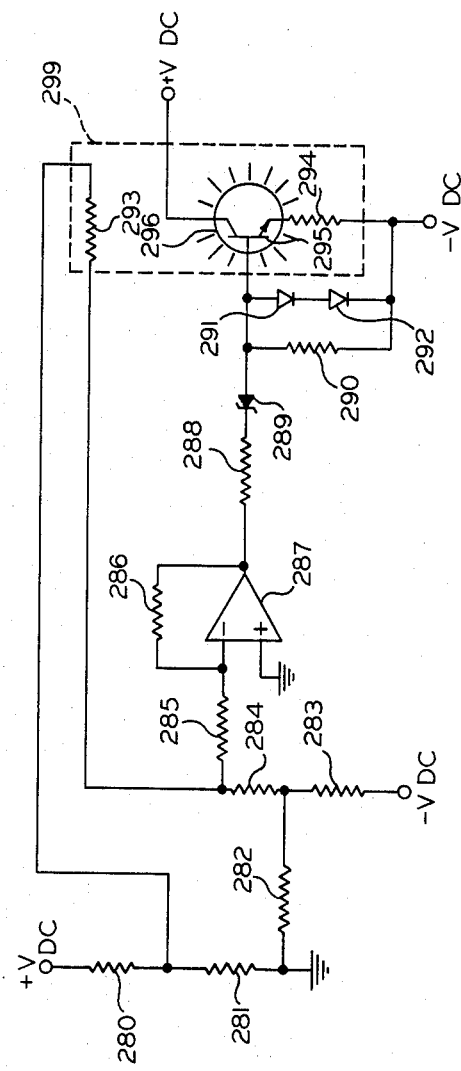
FIG. 7 is a schematic drawing of a card oven in accordance with one embodiment of the present invention.
Figure 8:
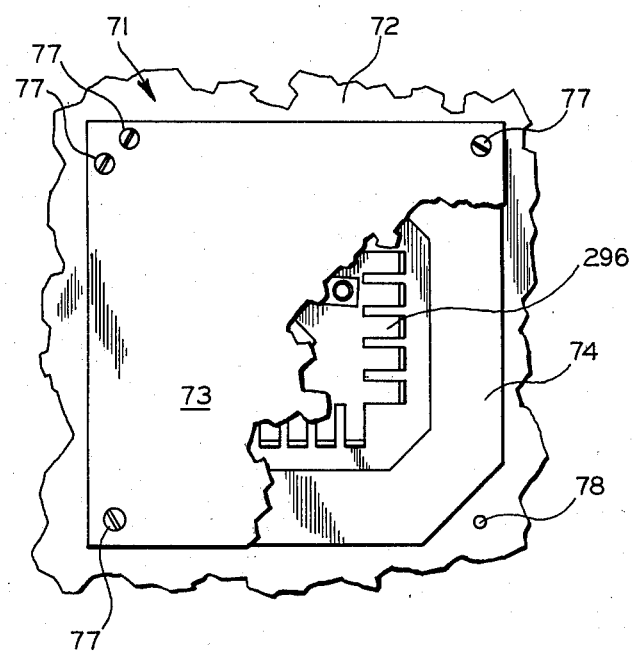
FIG. 8 is a perspective view of a mounted card oven having portions broken away to show structure.

The card oven according to our invention is shown in FIG. 7 and FIG. 8. FIG. 8 illustrates the card oven 71 mounted on the circuit board 72. Enclosure means are provided to enclose the components which are to be temperature stabilized when the oven 71 is mounted on card 72. The enclosure means in the illustrated embodiment comprises cover means 73 for covering the components to be temperature stabilized in the preferred embodiment logarithmic amplifier 303, and insulating means 74 preferably styrofoam for connecting the cover means to 73 the circuit board 72 for minimizing temperature changes. Cover means 73 can be a circuit board which carries the temperature control means circuitry shown in FIG. 7. The temperature control means in the illustrated embodiment comprises the circuit illustrated in FIG. 7 although equivalent circuits are also within the scope of the invention.

Resistor 280 has a first lead tied to a positive DC source, for example, −12 volts DC, and a second lead tied to a first lead of resistor 281 which has a second lead tied to ground. The first lead of resistor 281 is also tied to a first lead of thermistor 293. Thermistor 293 has a second lead tied to a first lead of resistor 285 and to a first lead of resistor 284. Resistor 284 has a second lead tied to a negative DC voltage source through resistor 283. Resistor 284 has a second lead also tied to ground through resistor 282.

Resistor 285 has a second lead tied to the inverting input of operational amplifier 287. The noninverting input of operational amplifier 287 is tied to ground. The output of operational amplifier 287 is tied back to the inverting input through resistor 286. The output of operational amplifier 287 is tied to the base of NPN transistor 295 through zener diode 289. The base of NPN transistor 295 is also tied to a negative DC voltage supply through a network comprising a resistor 290 connected in parallel to a first diode 291 and a second diode 292 connected in series. The emitter of NPN transistor 295 is also tied to the negative DC voltage source, for example, −15 volts DC through a resistor 294. The collector of NPN transistor 295 is tied to a positive DC voltage source, for example, +15 volts DC. Heat sink 296, shown also in FIG. 8, surrounds NPN transistor 295 and is functional for radiating heat therefrom, the transistor 295 and heat sink 296 acting as the heating element for the card oven.

The temperature of the oven can be preset by selecting the values of resistors 281, 282, and 284. Preferably, since the oven herein described has means only for heating, the preset temperature should be above anticipated ambient temperature. Thermistor 293 acts as a temperature sensitive device for controlling the current flowing through transistor 295. In the illustrated embodiment having component values as shown in Table III, the card oven can be maintained within about 1 degree Fahrenheit of the preset temperature of 140° F., i.e., at about 139 to about 141 degrees Fahrenheit to temperature stabilize the logarithmic amplifier 340.

Such temperature stabilization of the logarithmic amplifier 340 facilitates linearity in a chromatographic analyzer utilizing an optical absorbance detector for process applications where temperature variations can otherwise result in signal error.

The invention has been described in terms of its presently preferred embodiment as is shown in FIGS. 1 through 9. For the sake of convenience, signals which provide power to the various chips shown in the schematics of FIG. 5, FIG. 6, FIG. 7, and FIG. 8 have been omitted. Voltage levels required by the various chips are specified by the manufacturer and known by those familiar with the art.

Many different circuit configurations are possible which would perform the functions of the circuits shown in FIG. 5, FIG. 6, and FIG. 7. The circuits shown in FIG. 5, FIG. 6, and FIG. 7 are illustrative of a particular circuit configuration which will perform the required function.

Specific components which are available commercially and which can be used in the practice of the invention as shown in FIG. 1 through FIG. 9 inclusive follow. Values of discrete components, such as resistors and capacitors are also given. Again, many different combinations of circuit values, particularly in the areas of resistance and capacitance values, are possible.

TABLE III

| Component | Identification |
|---|---|
| FIG. 5 | |
| Resistors 272,262 | 1000 mΩ, MOX1125A, Victoreen |
| Capacitors 273,263 | 1000 pfd, DM-10-102J, Elmenco |
| Photodiode 212 | UV100B Dual Si., EG & G |
| Operational Amplifier 261,271 | 3528 BM, Burr-Brown |
| FIG. 6 | |
| Resistors 311,321,331 and 332 | 100 kΩ, RN55C1003F, Dale |
| Resistors 310 and 323 | 25.5 kΩ, RN55C2552F, Dale |
| Resistors 315 and 325 | 1.0 kΩ, RN55C1001F, Dale |
| Potentiometers 314,324 and 337 | 10 kΩ, 68XR10K, Helitrim |
| Resistor 338 | 1 mΩ, RN55C1004F, Dale |
| Resisitors 351 and 354 | 1.1 mΩ, ¼W, 5% |
| Resistors 353 and 363 | 1.6 mΩ, ¼W, 5% |
| Resistor 355 | 240 kΩ, ¼W, 5% |
| Resistor 358 | 2.4 mΩ, ¼W, 5% |
| Resistors 357 and 361 | 750 kΩ, ¼W, 5% |
| Potentiometer 339 | 20 kΩ, 68XR20K, Helitrim |
| Capacitors 359 and 364 | .22 μf, Z1X224K, ELPAC |
| Capacitors 356 and 352 | 4 μf, B1X405K, ELPAC |
| Diodes 312 and 322 | IN914, Fairchild Semiconductor |
| Operational Amplifiers 310 and 320 | OP-10EY, PMI |
| Operational Amplifiers 360 and 362 | TL062CP, Texas Instruments |
| Log Module 340 | 4127KG, Burr-Brown |
| FIG. 7 | |
| Resistors 280,283 and 288 | 1.2 kΩ, ¼W, 5% |
| Resistors 28, 282 | 100Ω, ¼W, 5% |
| Resistor 284 | 1.37 kΩ, RN55C1371F, Dale |
| Resistor 285 | 18 kΩ, ¼W, 5% |

TABLE III-continued

| Component | Identification |
|---|---|
| Resistor 286 | 10 mΩ, ¼W, 5% |
| Resistor 290 | 12 kΩ, ¼W, 5% |
| Resistor 294 | 5.1Ω, 1W, 5% |
| Thermistor 293 | 5 kΩ, K-678 |
| Zener Diode 289 | IN4739, Fairchild Semiconductor |
| Diodes 291 and 292 | IN914, Fairchild Semiconductor |
| Transistor 295 | TIP29C, Texas Instruments |
| Operational Amplifier 287 | MC1741, Motorola Semiconductor |

The following examples provide exemplary dimensions for various components of the detector as shown in FIG. 2, FIG. 3, and FIG. 4 to enable one familiar with art to practice the instant invention.

EXAMPLES

| | |
|---|---|
| Explosion proof housing 123 | |
| Cap portion 1231 | |
| length, inches | 5.625 |
| major diameter, inches | 3.75 |
| minor diameter, inches | 3.682 to 3.696 |
| threaded portion length, inches | 0.625 to 0.875 |
| Block 221 | |
| length, inches | 3.125 |
| width, inches | 1.750 |
| depth, inches | 1.468 |
| Chamber 228 in block 221 | |
| opening 233 diameter, inches | 0.703 |
| depth of chamber 228 | 3.100 |
| Chamber 230 | |
| chamber portion 2302 diameter, inches | 0.500 |
| chamber portion 2302 length, inches | 0.187 |
| chamber portion 2302 diameter, inches | 0.375 |
| chamber portion 2302 length, inches | 0.187 |
| aperture 208 diameter, inches | 0.063 |
| aperture 208 length, inches | 0.131 |
| Alignment holder 235 | |
| basal portion 2351 diameter, inches | 2.000 |
| sidewall portion 2352 length, inches | 1.250 |
| basal portion 2351 thickness, inches | 0.204 |
| Ring 2302 | |
| Outer diameter, inches | 0.495 |
| Inner diameter, inches | 0.375 |
| Length, inches | 0.125 |
| Cup 2033 | |
| spherical radius, inches | 0.375 |
| penetration in basal portion 2351, in. | 0.130 |
| aperture 2031 diameter, inches | 0.032 |
| aperture 2032 diameter, inches | 0.032 |
| distance between center of aperture 2031 and center of aperture 2032, inches | 0.164 |
| Alignment slot 236 | |
| width, inches | 0.126, i.d./0.128 o.d. |
| length, inches | 1.046 |
| Collimation Lens 204 | |
| diameter, inches | 0.500 |
| focal length, inches | 0.750 |
| spherical radius, inches | 0.375 |
| Flow cell 205 | |
| diameter, inches | 1.750 |
| length along longitudinal axis, inches | 0.394 |
| fluid light flow paths 206, 207 | |
| diameter, inches | 0.059 |
| length, inches | 0.394 |
| distance between center of flow path 206 to center of flow path 207 | 0.164 |
| alignment pin 238 diameter, inches | 0.1251 |
| Window 2088 | |
| diameter, inches | 0.500 |
| length, inches | 0.089 |
| Holder Filter 209 | |
| diameter, inches | 1.75 |
| length along longitudinal axis, in. | 0.300 |
| aperture 2091, 2092 | |
| diameter, inches | 0.086 |

EXAMPLES-continued

| | |
|---|---|
| length, inches | 0.061 |
| distance between center of aperture 2091 to center of aperture 2092, in. | 0.164 |
| cylindrical chamber 245 | |
| diameter, inches | 1.035 |
| length, inches | 0.150 |
| cylindrical chamber 2081 | |
| diameter, inches | 0.515 |
| length, inches | 0.089 |
| alignment pin 343 diameter, inches | 0.1251 |
| Interference filter 210 | |
| diameter, inches | 1.000 |
| depth, inches | 0.230 |
| Holder filter 211 | |
| diameter, inches | 1.750 |
| length, inches | 0.200 |
| cylindrical chamber 2121, | |
| diameter, inches | 0.500 |
| length, inches | 0.200 |
| cylindrical chamber 2102 | |
| diameter, inches | 1.750 |
| length, inches | 0.330 |
| apertures 2111, 2112 | |
| diameter, inches | 0.093 |
| length, inches | 0.04 |
| alignment pin 250, diameter, inches | 0.1251 |

A preferred embodiment of an optical absorbance detector in accordance with our invention has been described. The optical absorbance detector is rugged, compact, and capable of a linear dynamic range in the preferred embodiment between about $1 \times 10^{-4}$ and about 1.4 absorbance units with linearity within 1% for the preferred approximately 1 centimeter fluid light paths. The preferred embodiment chromatographic analyzer is particularly suitable for use in process applications characterized by high temperatures, the presence of inflammable vapors, and the like. Our invention is not to be considered limited to the preferred embodiment herein described, however, but by the claims hereinbelow appended.

That which is claimed is:

1. An optical absorbance detector comprising:
radiation point source means for producing a point source of light;
first spatial filter means optically aligned with the radiation point source means and operable for producing a first light beam and a second light beam, the first spatial filter means having an opaque portion thereof opaque to radiation from the radiation point source means, said opaque portion having a first through aperture and a second through aperture, the first through aperture and the second through aperture being optically aligned with the radiation point source means and the first through aperture allowing the first light beam to pass therethrough and the second through aperture allowing the second light beam to pass therethrough, the first aperture and the second aperture being separated by at least a portion of the opaque portion of the first spatial filter means;
collimating means in light communication with the first spatial filter means for collimating the first light beam to produce a first collimated light beam and for collimating the second light beam to produce a second collimated light beam;
first flow cell means for passing a first fluid through a first fluid light path optically aligned with the first collimated light beam to produce a first light signal representative of the first fluid;

second flow cell means for passing a second fluid through a second fluid light path optically aligned with the second collimated light beam to produce a second light signal representative of the second fluid;

first detector means for producing a first electrical signal representative of the first light signal;

second detector means for producing a second electrical signal representative of the second light signal; and a second spatial filter means, said second spatial filter means positioned between the first and second flow cell means and the first and second detector means and having an opaque portion opaque to the radiation from the radiation point source, said opaque portion having a first aperture therethrough being optically aligned with the first light signal and with the first detector means and a second aperture being optically aligned with the second light signal and with the second detector means.

2. An optical absorbance detector as in claim 1 wherein the radiation point source means comprises:
radiation source means for producing light; and
aperture means for allowing only a small amount of the thus produced light to pass therethrough.

3. An optical absorbance detector as in claim 2 wherein the aperture means comprises:
a block having a chamber therein for receiving the radiation source means, and
an emission aperture for allowing a small amount of light to pass therethrough, said emission aperture having a portion thereof generally circular in cross section.

4. An optical absorbance detector as in claim 3 wherein:
the collimating means comprises a collimating lens having a focal length generally equal to the distance between the emission aperture and the center of the collimating lens.

5. An optical absorbance detector as in claim 4 wherein:
each of the first aperture and the second aperture of the first spatial filter means has a diameter at least effective to allow sufficient light to pass therethrough to be respectively detected by the first detector means and the second detector means; and
said first aperture and said second aperture are separated by a separation distance such that less than 1% crossover can occur between the first light beam and the second light beam.

6. An optical absorbance detector as in claim 1 wherein:
the first detector means for producing a first electrical signal comprises a first photodiode for transducing the first light signal to an electrical signal and amplifier means having an input from said electrical signal and operable to amplify said electrical signal to produce the first electrical signal; and
the second detector means for producing a second electrical signal comprises a second photodiode for transducing the second light signal to an electrical signal and amplifier means having an input from said electrical signal and operable to amplify said electrical signal to produce the second electrical signal.

7. An optical absorbance detector as in claim 6 wherein:
the first photodiode and the second photodiode are supported on a common substrate.

8. Apparatus as in claim 1 further comprising:
difference signal means having a first input from said first electrical signal and a second input from said second electrical signal and operable for producing a difference signal representative of a difference in composition between the first fluid and the second fluid.

9. Apparatus as in claim 8 wherein the difference signal means comprises:
a first amplifier means having an input from the first electrical signal and operable for producing an amplified first electrical signal;
a second amplifier means having an input from the second electrical signal and operable for producing an amplified second electrical signal; and
logarithmic amplifier means having a first input from the amplified first electrical signal and a second input from the amplified second electrical signal and operable for producing a function signal representative of said difference in composition between the first fluid and the second fluid.

10. Apparatus as in claim 9 further comprising:
filter means having the function signal as a first input and operable for removing noise components greater than a preselected cut-off frequency from the function signal to produce the difference signal.

11. Apparatus as in claim 10 wherein:
the cut-off frequency is ⅛ Hertz.

12. Apparatus as in claim 10 wherein the logarithmic amplifier means is mounted on a printed circuit bond and is temperature stabilized by a card oven surrounding the logarithmic amplifier and mounted on said printed circuit board, said card oven comprising:
cover means for covering the logarithmic amplifier means;
insulating means connecting the cover means to the printed circuit board for forming an enclosure surrounding the logarithmic amplifier; and
temperature maintenance means for temperature stabilizing the thus surrounded logarithmic amplifier.

13. Apparatus as in claim 12 further comprising:
chromatographic analysis means for producing a first fluid representative of the composition of a carrier fluid stream to which sample has been added and for producing a second fluid representative of essentially only the carrier fluid;
first conduit means for connecting the first fluid in flow communication with the first fluid light path; and
second conduit means for connecting the second fluid in flow communication with the second fluid.

14. Apparatus as in claim 13 wherein:
the optical absorbance detector including the chromotographic analysis means, are enclosed in a temperature controlled oven; and
wherein the difference signal means is further enclosed in a purged enclosure.

15. Apparatus as in claim 14 wherein:
the optical absorbance detector is contained in an explosion resistant housing.

16. Apparatus as in claim 1 further comprising:
chromatographic analysis means for producing a first fluid representative of the composition of a carrier fluid stream to which sample has been added and for producing a second fluid representative of essentially only the carrier fluid;

first conduit means for connecting the first fluid in flow communication with the first fluid light path; and second conduit means for connecting the second fluid in flow communication with the second fluid.

17. An optical absorbance detector comprising:

radiation point source means for producing light;

a block having a chamber therein for receiving the radiation point source means; and an emission aperture for allowing a small amount of light to pass therethrough, said emission aperture having a portion thereof generally circular in cross section;

first spatial filter means optically aligned with the radiation point source means and operable for producing a first light beam and a second light beam, the first spatial filter means having an opaque portion thereof opaque to radiation from the radiation point source means, said opaque portion having a first aperture and a second aperture, the first aperture and the second aperture being optically aligned with the radiation point source means and the first aperture allowing the first light beam to pass therethrough and the second aperture allowing the second light beam to pass therethrough, the first aperture and the second aperture being separated by a separating distance of at least a portion of the opaque portion of the first spatial filter means; wherein each of the first aperture and the second aperture of the first spatial filter means having a diameter in the range of about 0.025 to about 0.045 inches; and the separating distance being at least 0.15 inches or greater;

collimating means in light communication with the first spatial filter means for collimating the first light beam to produce a first collimated light beam and for collimating the second light beam to produce a second collimated light beam;

the collimating means further comprising a collimating lens having a focal length generally equal to the distance between the emission aperture and the center of the collimating lens; and first flow cell means for passing a first fluid through a first fluid light path optically aligned with the first collimated light beam to produce a first light signal representative of the first fluid;

second flow cell means for passing a second fluid through a second fluid light path optically aligned with the second collimated light beam to produce a second light signal representative of the second fluid;

first detector means for producing a first electrical signal representative of the first light signal;

second detector means for producing a second electrical signal representative of the second light signal; and light path means for connecting the first light signal in light path communication with the first detector means and for connecting the second light signal in light path communication with the second detector means.

18. An optical absorbance detector as in claim 17 wherein:

each of the first aperture and the second aperture of the first spatial filter has a diameter in the range of about 0.031 to about 0.034 inches; and the separation distance is in the range of about 0.160 to about 0.170 inches.

19. An optical absorbance detector comprising:

radiation point source means for producing a point source of light;

a block having a chamber therein for receiving the radiation point source means; and an emission aperture for allowing a small amount of light to pass therethrough, said emission aperture having a portion thereof generally circular in cross section;

first spatial filter means optically aligned with the radiation point source means and operable for producing a first light beam and a second light beam, the first spatial filter means having an opaque portion thereof opaque to radiation from the radiation point source means, said opaque portion having a first aperture and a second aperture, the first aperture and the second aperture being optically aligned with the radiation point source means and the first aperture allowing the first light beam to pass therethrough and the second aperture allowing the second light beam to pass therethrough, the first aperture and the second aperture being separated by at least a portion of the opaque portion of the first spatial filter means;

collimating means in light communication with the first spatial filter means for collimating the first light beam to produce a first collimated light beam and for collimating the second light beam to produce a second collimated light beam;

first flow cell means for passing a first fluid through a first fluid light path optically aligned with the first collimated light beam to produce a first light signal representative of the first fluid;

second flow cell means for passing a second fluid through a second fluid light path optically aligned with the second collimated light beam to produce a second light signal representative of the second fluid;

first detector means for producing a first electrical signal representative of the first light signal;

second detector means for producing a second electrical signal representative of the second light signal; and a second spatial filter positioned between the first and second flow cell means and the first and second detector means and having an opaque portion opaque to radiation from the radiation point source, the opaque portion having a first and second aperture therethrough, the first aperture allowing at least a portion of the first light signal to pass therethrough, and the second aperture allowing at least a portion of the second light signal to pass therethrough;

interference filter means positioned between the second spatial filter and the first and second detector means for passing only a preselected band of wavelengths therethrough connected in light communication with the second spatial filter so that the portion of the first signal passing through the first aperture and the portion of the second signal passing through the second aperture are filtered through the interference filter means;

a third spatial filter means positioned between the interference filter means and the first and second detector means and having an opaque portion opaque to radiation from the radiation point source means and having a first aperture and a second aperture therethrough, the first aperture allowing at least a portion of the first light signal passing through the interference filter means to pass therethrough and the second aperture allowing at least a portion of the second light signal passing through the interference filter means to pass therethrough; and wherein the first detector means is optically aligned with the portion of the first light signal passing through the first aperture of the third spatial filter; and wherein the second detector means is optically aligned with the portion of the second light signal passing through the second aperture of the third spatial filter.

20. An optical absorbance detector as in claim 19 wherein:

the emission aperture has a diameter in the range of about 0.050 to about 0.070 inches;

the first aperture and the second aperture of the first spatial filter means each have a diameter in the range of about 0.025 to about 0.045 inches;

the first aperture and the second aperture of the first spatial filter means are separated by a separation distance in the range of about 0.150 to about 0.180 inches;

the first fluid light path and the second fluid light path each have a length of about one centimeter and each have a diameter in the range of about 0.03 to about 0.08 inches;

the first aperture and the second aperture of the second spatial filter means each have a diameter in the range of about 0.06 to about 0.10 inches; and the first aperture and the second aperture of the third spatial filter means each have a diameter in the range of about 0.080 to about 0.100 inches.

21. An optical absorbance detector as in claim 19 wherein:

the emission aperture has a diameter in the range of about 0.058 to about 0.065 inches;

the first aperture and the second aperture of the first spatial filter means each have a diameter in the range of about 0.029 to about 0.036 inches;

the first aperture and the second aperture of the first spatial filter means are separated by a separation distance in the range of about 0.160 to about 0.170 inches;

the first fluid light path and the second fluid light path each have a length of about one centimeter and each have a diameter in the range of about 0.045 to about 0.065 inches;

the first aperture and the second aperture of the second spatial filter means each have a diameter in the range of about 0.06 to about 0.10 inches; and the first aperture and the second aperture of the third spatial filter means each have a diameter in the range of about 0.080 to about 0.100 inches.

22. An optical absorbance detector as in claim 19 wherein:

the emission aperture has a diameter in the range of about 0.058 to about 0.065 inches;

the first aperture and the second aperture of the first spatial filter means each have a diameter in the range of about 0.031 to about 0.034 inches;

the first aperture and the second aperture of the first spatial filter means are separated by a separation distance in the range of about 0.160 to about 0.170 inches;

the first fluid light path and the second fluid light path each have a length of about one centimeter and each have a diameter in the range of about 0.055 to about 0.065 inches;

the first aperture and the second aperture of the second spatial filter means each have a diameter in the range of about 0.08 to about 0.09 inches; and the first aperture and the second aperture of the third spatial filter means each have a diameter in the range of about 0.090 to about 0.095 inches.

23. An optical absorbance detector comprising:

a lamp for emitting light;

an emission aperture optically aligned with the lamp;

a first spatial filter having an opaque portion opaque to the light of the lamp having a first aperture and a second aperture therein optically aligned with the emission aperture;

a collimating lens having a first portion optically aligned with the first aperture of the first spatial filter and a second portion optically aligned with the second aperture of the first spatial filter;

a flow cell having a first fluid light path optically aligned with the first portion of the collimating lens and further having a second fluid light path optically aligned with the second portion of the collimating lens;

a first detector optically aligned with the first fluid flow path;

a second detector optically aligned with the second fluid flow path;

a second spatial filter having an opaque portion opaque to light from the lamp and having a first aperture therethrough in optical alignment with the first fluid light path and further having a second aperture therethrough in optical alignment with second fluid light path;

an interference filter in optical alignment with the first aperture of the second spatial filter and in optical alignment with the second aperture of the second spatial filter;

a third spatial filter having an opaque portion opaque to light from the lamp and having a first aperture therethrough in optical alignment with the first aperture of the second spatial filter and with the interference filter and a second aperture therethrough in optical alignment with the second aperture of the second spatial filter and with the interference filter; and wherein:

the first detector is optically aligned with the first aperture of the third spatial filter and the second detector is optically aligned with the second aperture of the third spatial filter.

24. Apparatus as in claim 23 further comprising:

a source of carrier fluid;

a chromatographic column having an inlet and an outlet;

first conduit means for connecting the inlet of the chromatographic column in flow communication with the source of carrier fluid;

means for introducing a sample into the first conduit means;

second conduit means connecting the outlet of the chromatographic column in flow communication with the first fluid light path of the flow cell;

third conduit means connecting the source of carrier fluid in flow communication with the second fluid light path of the flow cell.

25. Apparatus as in claim 24 further comprising:

difference signal means having a first input electrically connected to the first electrical signal and a second input electrically connected to the second electrical signal and operable for producing a difference signal representative of a function of the first electrical signal and the second electrical signal.

26. Apparatus as in claim 25 wherein the difference signal means comprises:
first amplifier means having an input electrically connected to the first electrical signal and operable for producing an amplified first electrical signal;
second amplifier means having an input electrically connected to the second electrical signal and operable for producing an amplified second electrical signal;
logarithmic amplifier means having a first input electrically connected to the first electrical signal and a second input electrically connected to the second amplifier means, said logarithmic amplifier means being operable for producing a function signal representative of the logarithm of the first amplified electrical signal divided by the second amplified electrical signal;
filter means for filtering said logarithmic signal to produce the difference signal.

27. Apparatus as in claim 26 wherein the logarithmic amplifier means has a card oven to temperature stabilize temperature sensitive components.

28. Apparatus as in claim 26 wherein:
the difference signal means is enclosed in a purged gas enclosure;
the optical absorbance detector, including the chromatographic analysis means, are enclosed in a temperature controlled oven; and
the optical absorbance detector is enclosed in an explosion proof housing.

29. An optical absorbance detector comprising:
a block having a chamber therein for receiving a radiation source, the chamber having an emission aperture therein for allowing at least a portion of light emitted by the radiation source to leave the block;
an alignment holder having a basal portion and a sidewall portion, the basal portion being mounted on the block and further comprising a first spatial filter portion having an opaque portion opaque to radiation from the radiation source, the opaque portion having a first aperture and a second aperture therethrough optically aligned with the emission aperture, the basal portion further having a generally concave portion therein for at least partially supporting a collimating lens, and a sidewall portion having a plurality of openings therein;
a collimating lens optically aligned with the first aperture and the second aperture and having a generally convex portion and a generally planar portion, the generally convex portion being at least partially supported by the generally concave portion of the basal portion of the alignment holder;
a flow cell being generally cylindroid in conformation having a first generally planar surface and a second generally planar surface, and further having a first fluid light path and a second fluid light path extending between the first generally planar surface and the second generally planar surface, the first generally planar surface forming a fluid seal with the generally planar surface of the collimating lens and the flow cell further having first inlet means for passing fluid to the first fluid light path and first outlet means for removing fluid therefrom and second inlet means for passing fluid to the second fluid light path and second outlet means for removing fluid therefrom, said first fluid light path being optically aligned with the first aperture of the first spatial filter and the second fluid light path being optically aligned with the second aperture of the second spatial filter;
a window having a first generally planar surface forming a fluid seal with the second generally planar surface of the flow cell;
a first holder filter comprising means for at least partially supporting the window and further comprising a second spatial filter portion having an opaque portion opaque to radiation from the radiation source and having a first aperture therethrough optically aligned with the first fluid light path and a second aperture therethrough optically aligned with the second fluid light path, the holder filter further comprising means for attaching the holder filter to the block and first means for at least partially supporting an interference filter;
an interference filter at least partially supported by said first means for supporting an interference filter;
a second holder filter comprising second means for at least partially supporting an interference filter said second holder filter further comprising detector support means for at least partially supporting detector means for detecting light signals, and further comprising a third spatial filter having an opaque portion opaque to radiation from the radiation source and a first aperture therethrough optically aligned with the first aperture of the second spatial filter, the third spatial filter further having a second aperture therethrough optically aligned with the second aperture of the second spatial filter, said second holder filter further comprising means for mounting the second holder filter to the first holder filter; and
a light detector at least partially supported by the detector support means and having a first detector portion optically aligned with the first aperture of the third spatial filter and a second detector portion optically aligned with the second aperture of the third spatial filter.

30. Apparatus as in claim 29 further comprising:
alignment means for optically aligning the respective apertures of the alignment holder, the first holder filter, and the second holder filter.

31. Apparatus as in claim 29 wherein:
the emission aperture has a diameter in the range of about 0.050 to about 0.070 inches;
the first aperture and the second aperture of the first spatial filter means each have a diameter in the range of about 0.025 to about 0.045 inches;
the first aperture and the second aperture of the first spatial filter means are separated by a separation distance in the range of about 0.150 to about 0.180 inches;
the first fluid light path and the second fluid light path each have a length of about one centimeter and each have a diameter in the range of about 0.03 to about 0.08 inches;

the first aperture and the second aperture of the second spatial filter means each have a diameter in the range of about 0.06 to about 0.10 inches; and the first aperture and the second aperture of the third spatial filter means each have a diameter in the range of about 0.080 to about 0.100 inches.

32. Apparatus as in claim 29 wherein:

the emission aperture has a diameter in the range of about 0.058 to about 0.065 inches;

the first aperture and the second aperture of the first spatial filter means each have a diameter in the range of about 0.029 to about 0.036 inches;

the first aperture and the second aperture of the first spatial filter means are separated by a separation distance in the range of about 0.160 to about 0.170 inches;

the first fluid light path and the second fluid light path each have a length of about one centimeter and each have a diameter in the range of about 0.045 to about 0.065 inches;

the first aperture and the second aperture of the second spatial filter means each have a diameter in the range of about 0.06 to about 0.10 inches; and the first aperture and the second aperture of the third spatial filter means each have a diameter in the range of about 0.080 to about 0.100 inches.

33. Apparatus as in claim 29 wherein:

the emission aperture has a diameter in the range of about 0.058 to about 0.065 inches;

the first aperture and the second aperture of the first spatial filter means each have a diameter in the range of about 0.031 to about 0.034 inches;

the first aperture and the second aperture of the first spatial filter means are separated by a separation distance in the range of about 0.160 to about 0.170 inches;

the first fluid light path and the second fluid light path each have a length of about one centimeter and each have a diameter in the range of about 0.055 to about 0.065 inches;

the first aperture and the second aperture of the second spatial filter means each have a diameter in the range of about 0.08 to about 0.09 inches; and the first aperture and the second aperture of the third spatial filter means each have a diameter in the range of about 0.090 to about 0.095 inches.

* * * * *